United States Patent [19]

Mazess

[11] Patent Number: 5,228,068

[45] Date of Patent: Jul. 13, 1993

[54] DEVICE AND METHOD FOR AUTOMATED DETERMINATION AND ANALYSIS OF BONE DENSITY AND VERTEBRAL MORPHOLOGY

[75] Inventor: Richard B. Mazess, Madison, Wis.

[73] Assignee: Lunar Corporation, Madison, Wis.

[21] Appl. No.: 944,626

[22] Filed: Sep. 14, 1992

[51] Int. Cl.$^5$ ................. G01B 15/04; G01N 23/06
[52] U.S. Cl. ................................. 378/54; 378/55; 378/58
[58] Field of Search ............. 378/54, 51, 53, 55, 378/58, 62, 98; 364/413.13, 413.15, 413.19; 128/653.1

[56] References Cited

U.S. PATENT DOCUMENTS

| | | | |
|---|---|---|---|
| 4,788,429 | 11/1988 | Wilson | 378/53 |
| 4,811,373 | 3/1989 | Stein | 378/54 |
| 4,903,203 | 2/1990 | Yamashita et al. | 378/54 |
| 5,172,695 | 12/1992 | Cann et al. | 378/54 |

OTHER PUBLICATIONS

Current Research in Osteoporosis and Bone Mineral Measurement II: 1992, E. F. J. Ring, published by The British Institute of Radiology, London, 1992, pp. 14–16.
Change in Vertebral Shape in Spinal Osteoporosis, L. R. Hedlund, et al., Calcif Tissue Int (1989) 44:168–172.
A Comparison of Morphometric Definitions of Vertebral Fracture, Rebecca Smith-Bindman et al., Journal of Bone and Mineral Research, vol. 6, No. 1, 1991.
Guidelines for Clinical Trials in Osteoporosis, J. A. Kanis, et al., Osteoporosis Int (1991) 1:182–188.
Measurement of Vertebral Area on Spine X-Rays in Osteoporosis: Reliability of Digitizing Techniques, Journal of Bone and Mineral Research, vol. 5, No. 7, 1990.
A newly developed spine deformity index (SDI) to quantitate vertebral crush fractures in patients with osteoporosis, H. W. Minne, et al., Bone and Mineral, 3 (1988) 335–349.
Normal Vertebral Dimensions and Normal Variation in Serial Measurements of Vertebrae, Journal of Bone and Mineral Research, vol. 4, No. 3, 1989.
Pre-Existing Fractures and Bone Mass Precict Vertebral Fracture Incidence in Women, Philip D. Ross, PhD., et al. Jun., 1991, Annals of Internal Medicine.
A study of complaints and their relation to vertebral destruction in patients with osteoporosis, Gudrun Leidig, et al., Bone and Mineral, 8, (1990) 217–229.
Vertebral Morphometry in diagnosis of spinal fractures, L. R. Hedlund et al., Bone and Mineral, 5 (1988) 59–67.
Vertebral Morphometry: normative data, J. C. Gallagher, et al., Bone and Mineral, 4 (1988) 189–196.
Vertebral Deformity Indices: Influence of X-Ray Technique and Patient Width, Jan Willem Kuiper et al., Erasmus University Rotterdam.

(List continued on next page.)

*Primary Examiner*—David P. Porta
*Attorney, Agent, or Firm*—Quarles & Brady

[57] ABSTRACT

A method for the derivation of indicia of vertebral morphology from data obtained by lateral digital scans of the vertebrae obtains a matrix of data values assembled from a lateral vertebral scan. The matrix is analyzed to locate local minima and maxima from which the borders of the vertebral body may be calculated. Once the borders of the vertebral bodies are derived, one or more of several useful indicia of vertebral condition can be calculated. These indicia are associated with clinically recognized modes of vertebral condition. The data values in the matrix are also scanned for areas of unusual densities so that nonhomogeneous regions are not used in measuring overall bone mineral density of a vertebra.

18 Claims, 8 Drawing Sheets

OTHER PUBLICATIONS

Guidelines for Assessing Vertebral Fractures, Steve Cummings, Vertebral Fracture Workshop, Sep., 1992.

Nondisplaced Fractures: Spatial Resolution Requirements for Detection with Digital Skeletal Imaging 1, Mark D. Murphey, MD, et al., Department of Diagnostic Radiology, University of Kansas Medical Center, 1989.

Ability of Vertebral Dimensions from a Single Radiograph to Identify Fractures, Philip D. Ross et al., Calcif Tissue Int. (1992) 51:95–99.

Normal Vertebral Body Size and Compressive Strength: Relations to Age and to Vertebral and Iliac Trabecular Bone Compressive Strength, Bone 7, 207–212 (1986).

Bone mineral mass associated with postmenopausal vertebral deformities, J. E. Harrison, et al., Bone and Mineral, 10, (1990) 243–251.

The spine deformity index in osteoporosis is not related to bone mineral and ultrasound measurements, Peter Bernecker, M.D., 1992, The British Journal of Radiology, 65, 393–396.

Vertebral Fracture or Vertebral Deformity?, Calcif Tissue Int (1992) 50:5–6.

Atlas of Roentgenographic Measurement, pp. 225–226, 233–234, 236–237, 264–267.

Spine Deformity Index (SDI) Versus Other Objective Procedures of Vertebral Fracture Identification in Patients with Osteoporosis: A Comparative Study, Peter Sauer, et al., Journal of Bone and Mineral Research, vol. 6, No. 3, 1991.

DEVICE AND METHOD FOR AUTOMATED DETERMINATION AND ANALYSIS OF BONE DENSITY AND VERTEBRAL MORPHOLOGY

FIELD OF THE INVENTION

The present invention relates to the general field of bone densitometry and vertebral morphology and relates, in particular, to an automated technique and apparatus for the determination and analysis of vertebral morphology utilizing techniques of bone densitometry.

BACKGROUND OF THE INVENTION

Digital bone densitometry devices such as the DPX machines manufactured by LUNAR Corporation of Madison, Wis. or the QDR machines manufactured by Hologic, Inc. of Waltham, Mass., are used to generate broadly based values of bone character, such as bone mineral content ("BMC") or bone mineral density ("BMD"). Such information about bone character, and in particular, about bone character in the spine is often relied on to diagnose and treat bone depletive disorders such as osteoporosis. In the case of osteoporosis, bone density measurements alone are not definitive for diagnosis. The clinician must also look for evidence of spinal fracture J A. Kanis et. al. Osteoporosis Int. 1:182-188 (1991). Determining whether a fracture is present is important on clinical grounds and for research purposes. In the clinical setting, a patient may display a reduced BMD but the clinician is hesitant or unwilling to begin a particular treatment regimen without a diagnosis of fracture or deformity. In the research setting, diagnosis of fracture is important in studying the incidence and prevalence of osteoporosis in a population, or as an entry criterion to a clinical study, or as a measure of efficacy with regard to a particular treatment. In this regard, the European Foundation for Osteoporosis has published guidelines for clinical trials in osteoporosis which recommends a definition of osteoporosis as a "disorder where one or more fractures has arisen due to an increase in the fragility of bone," and an endpoint of fracture reduction in studies of efficacy of new drugs for the treatment of osteoporosis. J. A. Kanis, et. al.

While the presence or absence of vertebral fracture is critical in the diagnosis of osteoporosis, diagnosis of vertebral fracture is often difficult. Over one-half of such fractures are asymptomatic, and in cases of minimal symptoms obvious fracture or deformity will often not be observed particularly if there is no previous radiological record for comparison.

Vertebral morphometry techniques promise to make the determination of vertebral fracture or deformation more objective. These approaches rely on certain indexes or normative values of vertebral body dimensions. See e.g. Minne et al., "A Newly Developed Spine Deformity Index (SDI) to Quantitate Vertebral Crush Factors in Patients with Osteoporosis," *Bone and Material*, 3:335-349 (1988); J. C. Gallagher et al, "Vertebral Morphometry: Normative Data," *Bone and Mineral*, 4:189-196 (1988); Hedlund et al, "Vertebral Morphometry in Diagnosis of Spinal Fractures," *Bone and Mineral*, 5:59-67 (1988); and Hedlund et al, "Change in Vertebral Shape in Spinal Osteoporosis," *Calcified Tissue International*, 44:168-172 (1989).

In using vertebral morphometry to diagnose fractures, the clinician commonly employs analog radiological imaging techniques. In essence, an analog x-ray image of the patient's vertebrae is taken, and printed onto a fixed media, such as an x-ray radiographic film print. The print is made to a specific scale relative to the original human, i.e., one-to-one, or a specifically reduced or expanded scale. Then the clinician manually measures the size of a vertebra by using a ruler and a straight edge and actually draws on the film to outline the vertebral body, and then measures with the ruler between criteria lines drawn onto the film itself.

There have been recent efforts to computerize this morphometric technique. See e.g. Nelson, et. al., "Measurement of Vertebral Area on Spine X-rays in Osteoporosis: Reliability of Digitizing Techniques", *J. Bone and Mineral Res.*, Vol. 5, No. 7:707-716 (1990); Smith-Bindman et. al., "The index of radiographic area (IRA): a new approach to estimating the severity of vertebral deformity", *Bone and Mineral*, 15:137-150 (1991). These efforts still rely on first obtaining an analog X-ray image of the vertebra, digitizing the analog image and then manually selecting the points of measurement.

Thus the clinician diagnosing or treating osteoporosis must, at a minimum, use two relatively expensive medical devices: a bone densitometer and an X-ray imaging device. Further, morphometric techniques which rely on analog radiography are complicated by image magnification. The analog radiographic image is typically 10-15% larger than life-size, and the magnification is variable depending on the location of the object relative to the plane of the radiograph. In particular, the front edge of the object, away from the radiographic plate is more magnified than the back edge toward the radiographic plate. The result is that bone edges perpendicular to the plane of the plate, which for morphological measurement should produce a sharp visual demarcation on the fan beam radiograph produce a blurred boundary. Distortions of the spine are particularly acute for cone beam exposures at the edges of the cone beam where the beam is most angled. For vertebral morphology the angulation obscures and distorts intervertebral spacing at the top and bottom of a field rendering morphological measurements, for example of body height, imprecise. This impreciseness is exacerbated by the imposition of human error when it is left to the clinician to manually select the measurement point. Variation will often necessarily exist between clinicians and between measurements by the same clinician at different times.

While bone densitometers such as the DPX and the QDR devices are capable of generating images, the image quality of these present day bone densitometers is inferior to the common analog X-ray imaging machine. This is particularly true for scanning systems where resolution is intentionally limited to prevent the need for an overly long scanning time. Thus, the imaging capability of bone densitometers has not been relied on for diagnostic purposes and until the present invention, bone densitometry systems have not been used to determine bone morphology, or to analyze the relationships of bone structures.

SUMMARY OF THE INVENTION

The present invention is for a new technique and apparatus for the determination and analysis of vertebral morphology utilizing techniques of densitometry. More specifically, the invention will permit the determination of BMC and BMD in addition will determine and analyze vertebral morphology for use in diagnosis of certain conditions of vertebral deterioration including osteoporosis. The invention utilizes the digital information obtained by the techniques of densitometry and applies a new technique to organize this information into a usable form so that morphometric determinations of the vertebral body can automatically be made. More specifically, a new computer program samples and organizes the digital data values obtained from a lateral scan of a vertebral body into a rectangular matrix having a size and orientation corresponding to the size and orientation of the vertebral body under study. The program automatically selects measurement zones within the matrix which correspond to anterior, middle and posterior portions and the superior, central and inferior portions of the vertebral body and applies an algorithm to calculate the average height of each region. The program then automatically compares the average height measurements to a preselected index or normative standard. Using the invention, indicia associated with significant clinical conditions of the human spine can be reliably produced. As explained in more detail below, the morphometric determinations will also improve the diagnostic interpretation of the BMD measurements which will tend to be increased by bone compaction when a vertebra is fractured.

It is thus an object of the present invention to provide a technique and apparatus for reliable and reproducible analysis of vertebrae in vivo which permits the early clinical detection of certain potential pathological conditions of vertebral change.

It is yet another object of the present invention to provide a semi-automated or automated technique and apparatus for determination and analysis of bone character and bone morphology.

It is yet another object of the present invention to improve the interpretation and accuracy of vertebral bone density measurements by providing morphometric information about the vertebra being studied.

Other objects, advantages, and features of the present invention will become apparent from the following specification when taken in conjunction with the accompanying drawings.

DESCRIPTION OF THE PREFERRED EMBODIMENT

The present invention is directed toward a device and method for automatically obtaining measurements of bone character and morphometry of a vertebral body of a human or animal. In the preferred embodiment, an X-ray beam is used for the measurements of bone character (i.e. BMC and BMD) whereas a single energy X-ray beam is used for the morphometric measurements. It has been determined that the single energy beam provides greater precision (i.e. higher data density per pixel) in the resulting scan than a dual energy system. However, the novel features of the invention can also be combined with the features of strictly dual energy X-ray densitometers to permit measurement of the morphometry as well as the bone density of the subject.

For purposes of illustrating the present invention, a study of the morphology of a human vertebra will be described. It should be understood, however, that the invention is not limited to studies of humans but can be applied to animals as well as humans.

Figure 1:
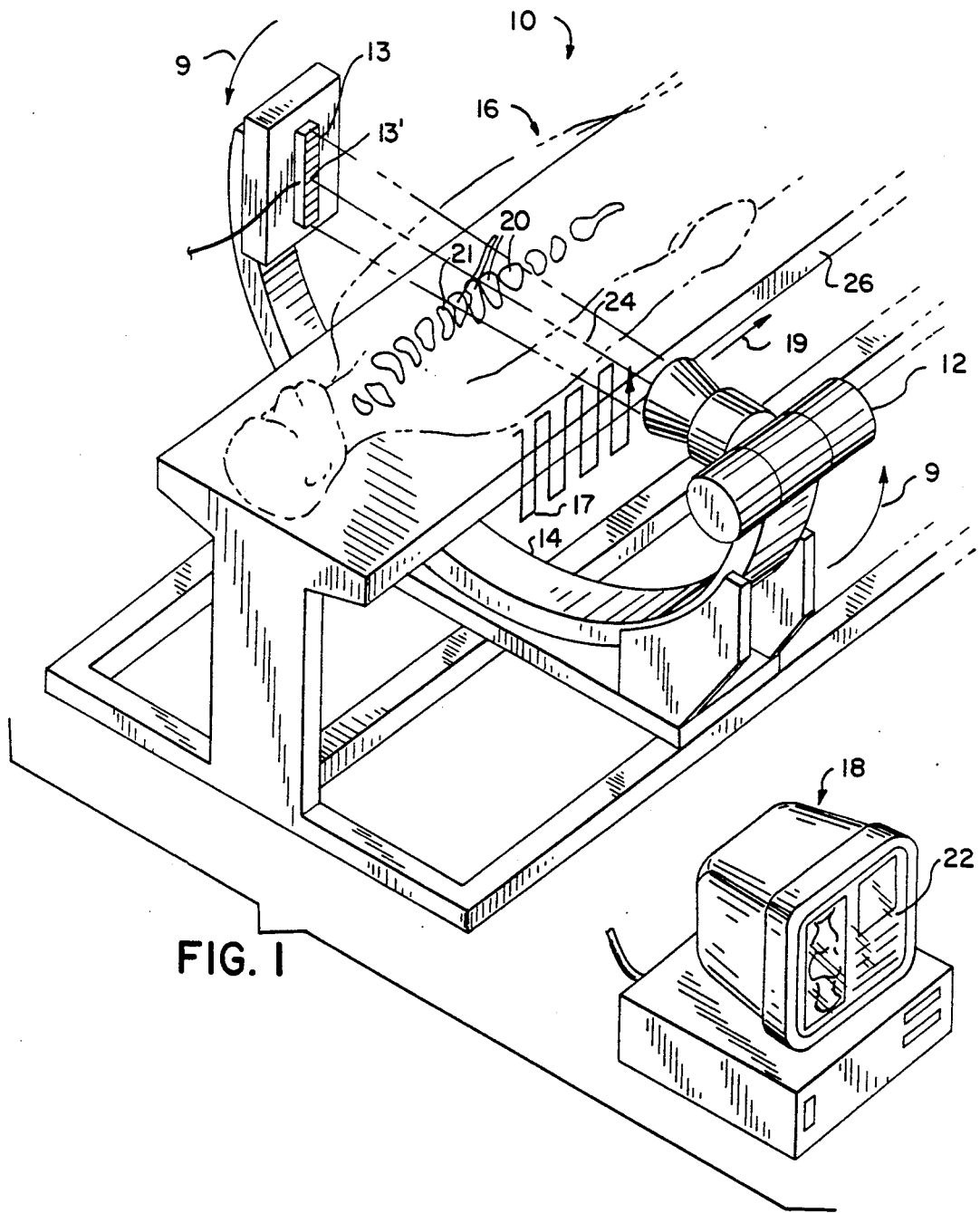
FIG. 1 is a schematic illustration of an instrument for use in the present invention showing a first embodiment employing a pencil bean and a raster scan and a second embodiment employing a fan bean and a linear scan.

Shown in FIG. 1 is a simplified schematic of a X-ray based densitometer 10 of the type described in the preferred embodiment of the present invention. The instrument 10 includes a dual energy X-ray radiation source 12 and a detector 13, both of which are mounted on a rotatable C-arm 14, which extends on either side of a supine patient 16 so as to direct and receive radiation along a radiation axis 24 through the patient 16. The C-arm 14 is designed to be rotated in a vertical plane as indicated by arrows 9 so as to allow both an anterior-posterior ("AP") view of the spine and a lateral view of the spine. The C-arm 14 may also be moved longitudinally along the patient's body as indicated by scanning direction arrow 19 and may be positioned under the control of servo motors as is understood in the art.

The densitometer 10 of the preferred embodiment, has the capability of switching from a dual energy X-ray to a single energy X-ray or polychromatic X-ray mode. By single-energy X-ray is meant ionizing radiation at a narrow band of energies of a few keV in the diagnostic imaging range (20–100 keV) or a polychromatic beam such as is conventionally emitted from an X-ray source. Switching from dual energy to single energy may be done either by affecting the source, e.g., removing or adding a K-edge filter, or by switching energies, i.e., switching between high and low x-ray tube voltage, or by affecting the detector e.g. selecting only one energy level during a particular study, or a combination of source and detector.

The densitometer 10 of the preferred embodiment also has the capability of selecting between a fan beam of x-rays which is collimated and oriented toward the vertebra such that the plane of the fan beam and detector is perpendicular to the longitudinal axis of the spine or a pencil beam being substantially the centermost ray only of the fan beam along the radiation axis 24. When the fan beam configuration is selected, the detector 13 is a linear array of detector elements subtending the fan beam for providing simultaneous measurements along a number of rays of the fan beam associated with each such detector element. When the pencil beam configuration is adopted, only the centermost detector element 13, is employed and measurement is made only along the single ray of the pencil beam. A cone beam (not shown in FIG. 1) may also be used, in which case the detector 13 is matrix of rows and columns of detector elements covering the area of the fan beam opposite the patient 16.

The fan beam, when used, is scanned along the @longitudinal axis of the spine or scanning axis 19. The use of a narrow fan beam perpendicular to the spine allows imaging of the spine with minimal distortion along the longitudinal axis resulting in the ability to measure vertebral dimensions in this axis with greater accuracy than possible with a cone beam. For greater accuracy in the horizontal axis, the fan beam may also be oriented so that the vertebral body is irradiated by the center portion of the beam rather than the edges which are subject to distortion. Since the center of a fan beam has little angulation the resulting data is comparable to that obtained with a pencil beam and yet a scan can be obtained much faster.

Alternatively, when the pencil beam is used a raster scan 17 of the lateral view of the vertebral body is done. The raster scan moves the radiation axis back and forth in the anterior posterior direction along successive scan lines separated in the longitudinal direction so that the radiation axis moves generally along the scan direction 19. The raster scan 17 results in the slower acquisition of data but provides the least distortion.

If a cone beam is used, the digital output must be reformatted to compensate for ray alignment in order to allow more accurate measurement of dimension. The cone beam acquisition may be performed at discrete stationary locations or may be acquired continuously as the radiation axis 24 is scanned along the scan direction 19. In studying the morphometry of the human vertebra, the scan is preferably taken from the side of the patient 16, so as to provide a lateral scan of the vertebrae 20 of the patient 16 and the single energy X-ray mode is selected. The rotatable C-arm 14 carrying the radiation source 12 and the detector 13 is connected to, and operates under the control of, a general-purpose digital computer 18, which is specifically programmed for use in operating the instrument 10 and analyzing the data and includes specialized algorithms for carrying out the calculations required by the present invention. In addition, the present invention includes a data acquisition system ("DAS") and a data storage device (both of which are not shown) and may be included in the computer 18 and a display means 22 for outputting the data analysis.

In most general terms, the radiation source 12 emits radiation of a certain energy level or levels along the radiation axis 24 at defined locations along the scan. The radiation passes through the vertebral body 21 being scanned and is then received by the detector 13. The analog output of the detector 13 is sampled and digitized so as to produce a signal consisting of discrete data elements by a data acquisition system ("DAS") which may then transmit the digitized signal to the computer 18 which stores the data in computer memory (not shown) or on a mass storage device.

Figure 5:
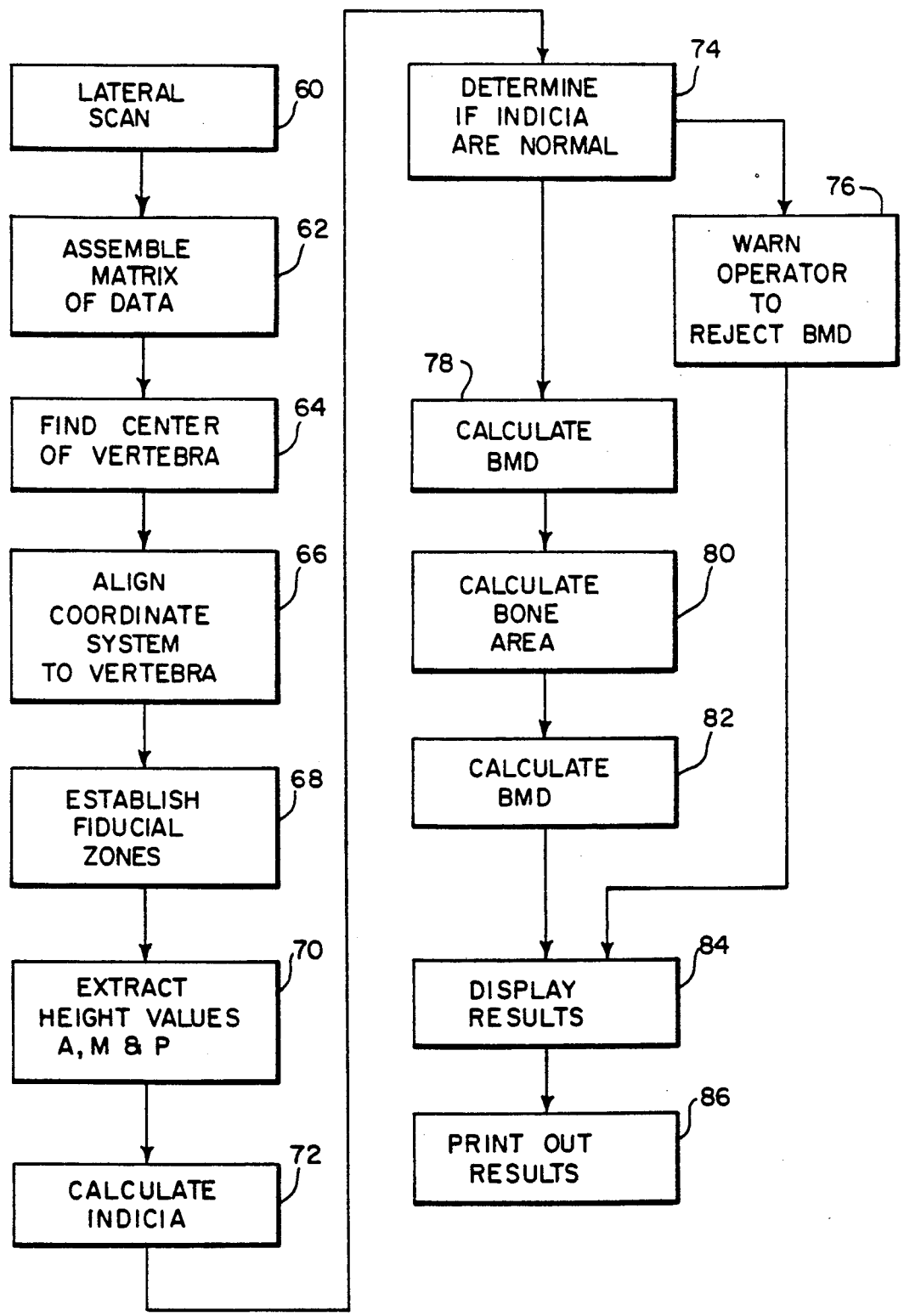
FIG. 5 is a flow chart illustrating the method of the present invention.

As can be seen by reference to FIG. 5, once scanning of the patient 16 by the source 12 and detector 13 are completed, as indicated by process block 60, the computer 18 of the present invention arranges the data elements obtained in the scan in a matrix per process block 62. Each data element of the matrix is associated with a spatial location defined by the position of the C-arm@ 14 when the data element is acquired during the scan. The spatial locations among the data elements differ by the distance the instrument, e.g., the source 12 and detector 13, moves between taking each data point, both laterally and (in the case of the pencil beam) vertically between scans.

For an instrument 10 such as that in FIG. 1 which uses a fan beam, data elements are taken in a series of scans by moving the X-ray source 12 and detector 13 in short longitudinal steps. If a pencil beam is used, data elements are taken in short vertical scans in the anterior-posterior direction. In either case the matrix of data elements is assembled from a series of these scans to collect data over an area defined by the length of the scan along the longitudinal scanning 19 or the vertical lines of the raster scan 17.

In studying the morphology of the human vertebra, it is preferred that the scan be taken from a lateral direction through the subject's spine. Each data element has a relative value proportional to the amount of radiation absorbed by the tissue at the corresponding location. In turn, the absorption of radiation by a tissue correlates to certain physical properties of that tissue. For example, bone absorbs a lesser amount of radiation than does soft tissue. The data elements thus obtained, are referred to PBM for pseudo bone mineral content. The numbers are pseudo values because they are non-calibrated and therefore dimensionless. At this point in the analysis, therefore only the relative differences between the data elements are significant, not their absolute values. While the calibration for each data element could be done at this point, it is consumptive of computer resources, and thus is deferred at this point and the PBM values are used. The matrix of values thus obtained is a representation of the relative density of the patient's vertebra viewed laterally.

Once the matrix is assembled, the computer 18 automatically conducts a local comparison of data elements to determine the juncture of data elements attributable to bone and data elements attributable to soft tissue. In order that the purpose and the results obtained from such a scan may be readily understood, reference is had to FIG. 2 which illustrates an idealized set of vertebrae 20. Each of the vertebrae 20 has characteristic boundary regions indicated by the reference numbers in FIGS. 2 with respect to a single vertebra. Each of the vertebrae has an anterior border 30, a posterior border 32, a superior border 34, and an inferior border 36. Additional elements of the vertebrae 20 located rearward of the posterior border are referred to as the posterior elements 38. The region between adjacent vertebrae 20 is referred to as the intervertebral zone and is indicated at 40.

Superimposed on the lowest of the illustrated vertebrae 21 of FIG. 1 is a series of horizontal lines, representing the raster scans 17 of the instrument 10 as employed when the instrument 10 is operating with a pencil beam. The results of that raster scan is the matrix of digital values, with each point value in a single scan being displaced one unit distance from the previous measured digital value.

Figure 2:
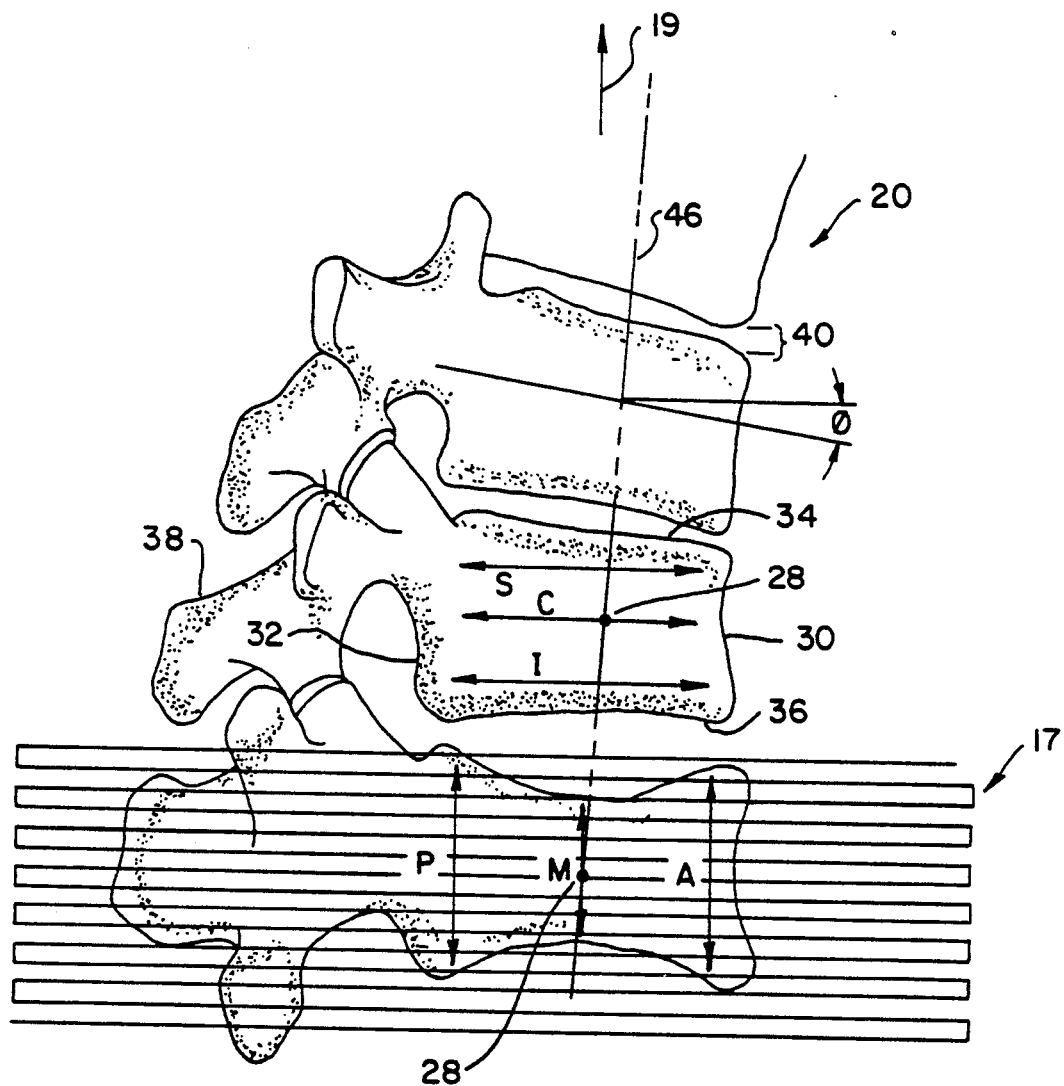
FIG. 2 is an illustration of a lateral view of a vertebra illustrating measurements used in determining the indicia used in the present invention.

Referring to FIGS. 1 and 2, the patient 16 is supported in the supine position on a table 26 so that the vertebrae 20 of the spine are generally aligned with the scan direction 19. Nevertheless, it will be recognized that because of the curvature of the spine, the angle of the vertebrae 20, i.e., the angle of the anterior border 30, a posterior border 32, a superior border 34, and an inferior border 36 with respect to the scan direction 19 will vary among vertebrae 20. Whereas this variation may be accommodated by the trained eye of a physician in estimating the distances that describe the morphology of the vertebrae 20, for the automation of such measures, the orientation of the vertebral body 21 with respect to the raster 17 or the scan direction 19 must be established to provide repeatable and accurate morphology measurements.

The first step in evaluating the relative placement of a vertebral body 21, indicated by process block 64 of FIG. 5, is a determination of the approximate location of each vertebrae 20 as identified by its approximate center 28. The centers 28 are located by evaluating the horizontal and vertical histograms of FIGS. 3 and 4.

Figure 4:
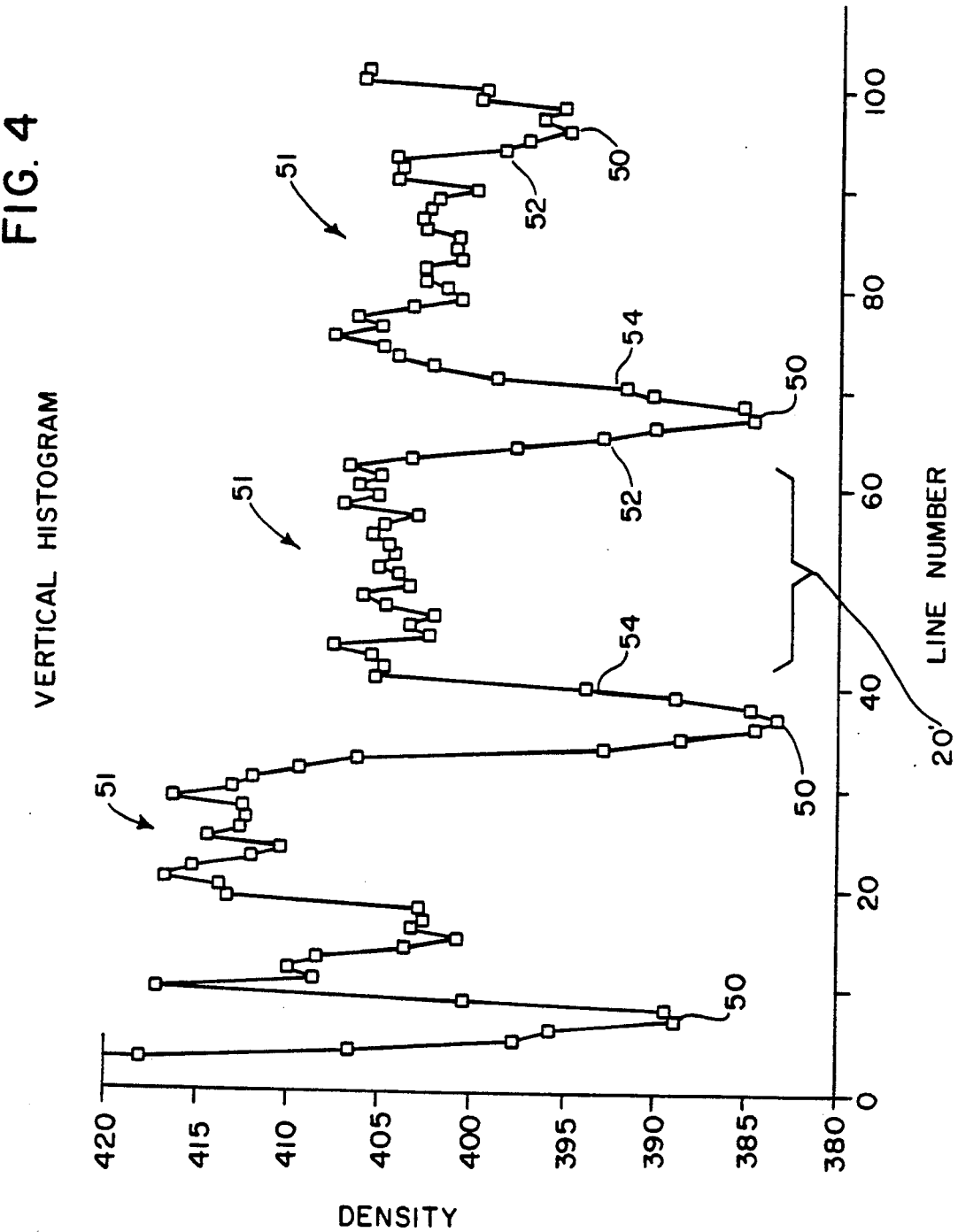
FIG. 4 is a histogram illustrating a set of data points in a vertical cross-section of a vertebra.

Shown in FIG. 4 is a superior-inferior histogram of the spinal column of vertebrae 20. The vertical axis of the histogram represents the units of body density measured at the detector 13 while the horizontal axis represents the spatial locations of data elements along a line such as indicated at 46 in FIG. 2. Ideally, line 46 is centered along the spine as positioned by several arbitrary horizontal histograms of adjacent vertebrae 20 as will be described below. Alternatively, the histogram of FIG. 4 may represent not the data elements along a single line 46 but an average of data elements along anterior-posterior lines.

Generally, when a pencil beam is used, the data elements in the vertical histogram are not derived from a single line of raster scan 17 of instrument 10 but rather are reassembled using suitable digital techniques from the entire matrix of data elements collected by the instrument 10. As reassembled, the values of the histogram of FIG. 4 represent a sequential series of data elements taken in a superior-inferior direction. This set of data elements is equivalent to the result which would be obtained from a single superior-inferior scan.

Note that the histogram of FIG. 4 includes local minima 50 and local maxima 51. These minima 50 represent areas of low density and the maxima 51 represent areas of high density. The location of the intervertebral zones 40 are readily ascertainable as the local minima 50 and the approximate inferior border 52 and superior border 54 of the vertebrae 20 are recognizable as the portions of the histogram on either side of the local minima 50. The superior-inferior centers of the vertebrae may be identified as points halfway between the local minima 50.

Figure 3:
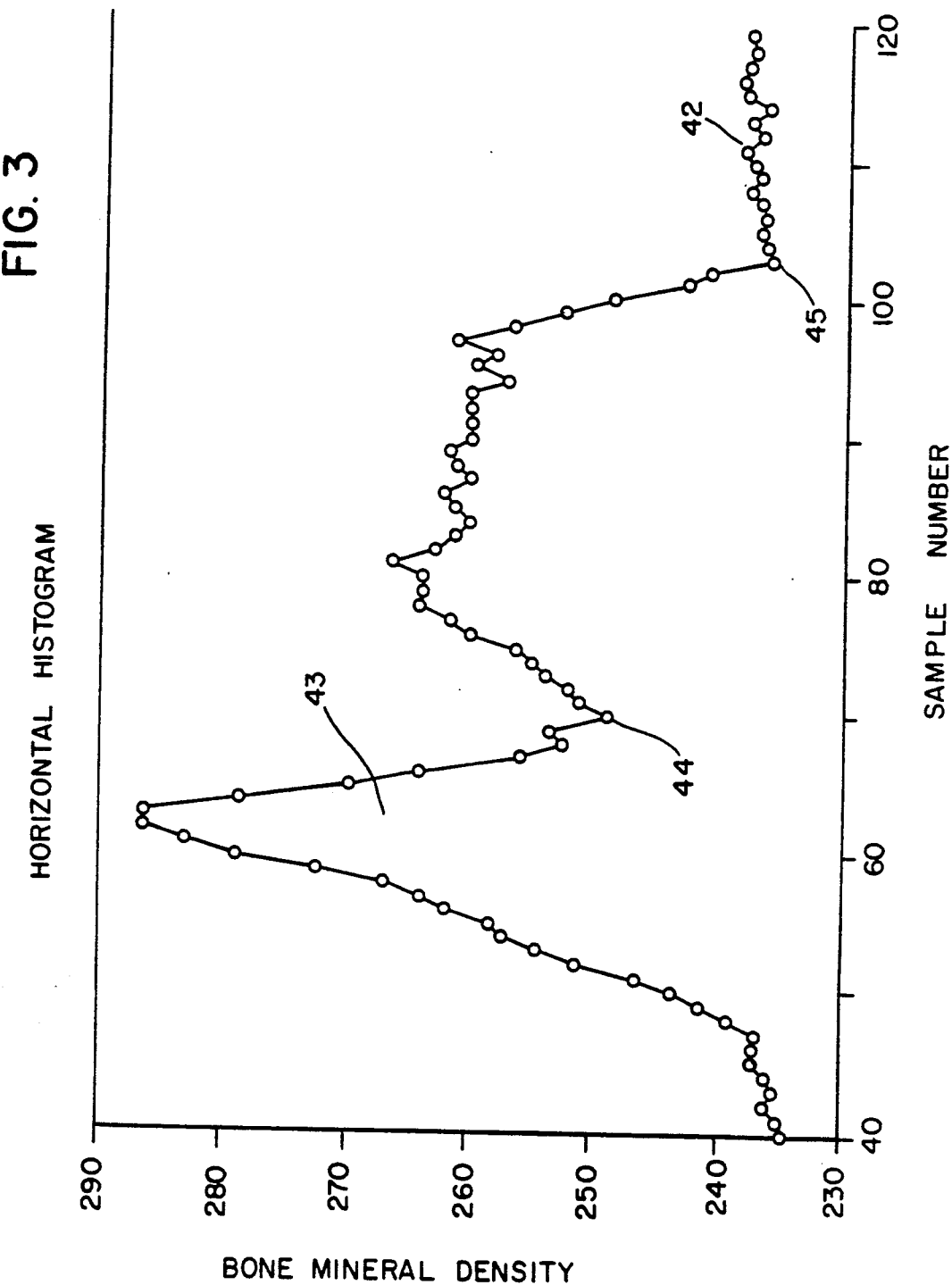
FIG. 3 is a histogram illustrating a set of data points in a horizontal scan of a vertebra such as that illustrated in FIG. 2.
Figure 6:
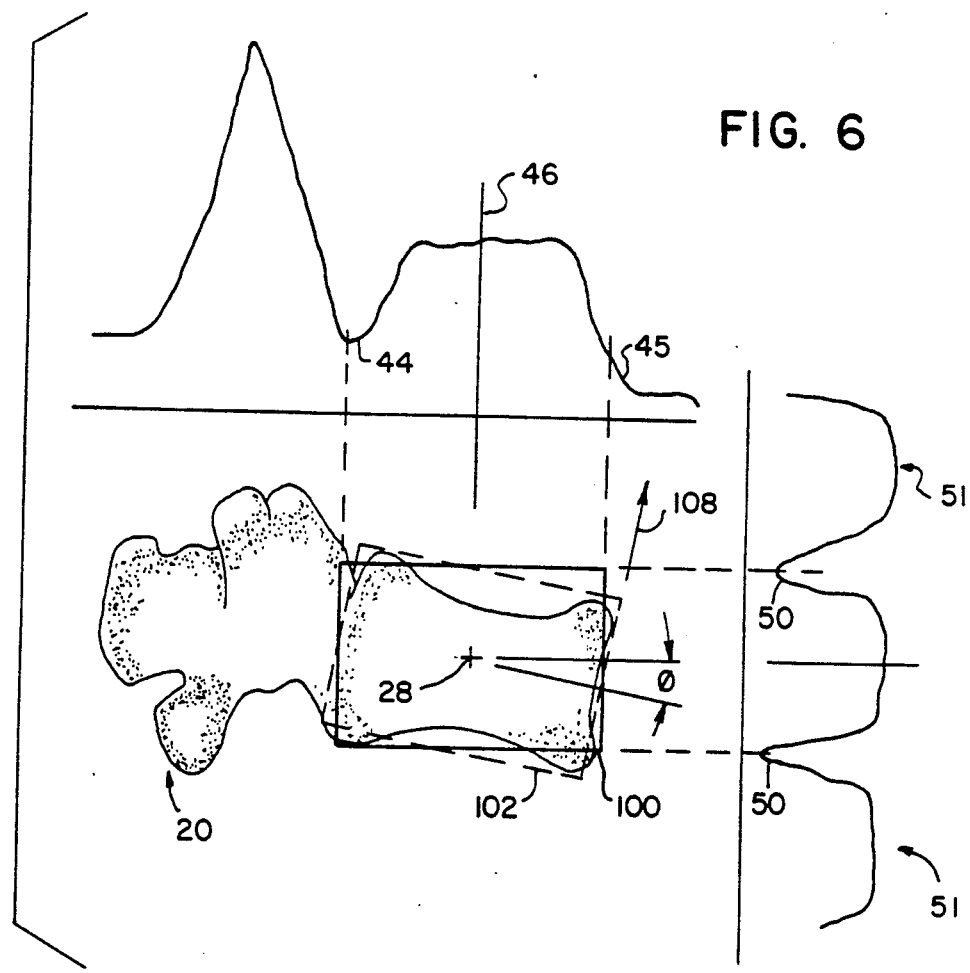
FIG. 6 is an illustration of a vertebra and its vertical and horizontal histograms similar to FIGS. 2, 3 and 4 showing a first method of determining an analysis axis.

Referring now to FIG. 3, a horizontal histogram is constructed along each anterior-posterior line of the scan pattern. The horizontal histogram of FIG. 3, like the vertical histogram of FIG. 4, has as its vertical axis bone mineral density. The horizontal axis of the histogram of FIG. 3 is the number of an anterior-posterior scan line. Also like the vertical histogram of FIG. 4, the horizontal histogram has local minima 44. The local minimum 44 represents the approximate posterior border 32 of the vertebra 21 located between the maxima created by the posterior elements 38 and the maxima created by the major portion (i.e. the body) of the vertebra 21 itself. Minimum 45 indicates the approximate anterior border of the vertebra 21. Thus the center 28 of each vertebrae 20 may be approximated as illustrated in FIG. 6 as the intersection of the scan line in the anterior-posterior direction which is halfway between points 44 and 45 and the superior-inferior center 53 of the vertebra 21 which is halfway between the local minimum 50 of the vertical histogram.

Referring now to FIG. 5, once the center 28 of each vertebrae 20 has been detected as indicated by process block 64, a coordinate system is established aligned to each vertebrae 20. Referring now to FIG. 6, a rectangular area 100 may be established about the center 28 of each vertebrae 20 having an anterior-posterior width equal to the distance between minima 44 and 45 and having a superior-inferior height equal to the distance between minima 50. As defined, the rectangular area 100 will be aligned with its sides parallel or perpendicular with the scans of raster scan 17 or the scan direction 19.

The PBM data elements within the rectangular area 100, are then summed to produce an alignment value. This alignment value indicates roughly the total bone mass of the vertebral body 21 within rectangle 100 and is thus a general measure of the "fit" of the rectangle 100 to the vertebral body 21.

A new rectangle 102 is then created also centered about point 28 but perturbed by angle $\phi$ and a new alignment value is calculated. If the perturbed rectangle 102 produces a lower alignment value, a new perturbed rectangle 102 is generated with a rotation in the opposite direction. If, however, a higher alignment value is obtained with perturbed rectangle 102, a further rectangle 102 is generated with additional angle $\phi$ and a new alignment value calculated. This process is repeated until there is detected a decrease (after an increase) in alignment value within the perturbed rectangle 102.

Thus, rectangle 102 is gradually rotated in one way or the other until the alignment value is maximized. It is found that the orientation of rectangle 102 which gives the highest alignment value is also the orientation which maximizes the amount of vertebral body 21 contained within borders of rectangle 102. Thus, upon completion of the rotation process, the rectangle 102 is a best fit of a rectangle 102 to the vertebral body 21 and establishes a coordinate system for analyzing the vertebral body 21 morphology. Specifically, all measurements of the vertebral body 21 are taken along parallels to the vertical or horizontal edges of the rectangle 102. A column axis 108 parallel to the vertical edge of rectangle 102 is identified to indicate this axis of measurement as distinguished from the scan direction 19.

Figure 7:
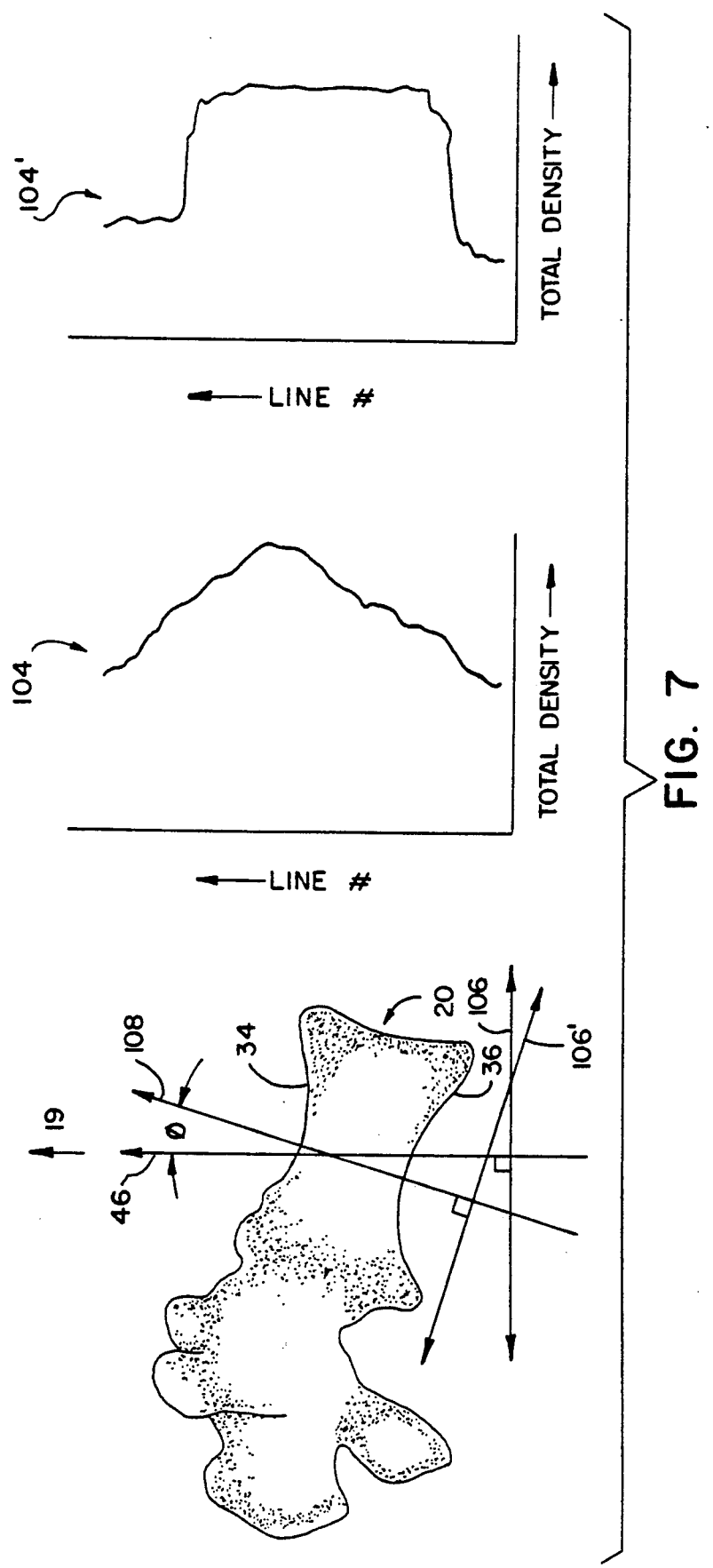
FIG. 7 is an illustration of a vertebra showing corresponding histograms taken along two different axes showing a second method of determining an analysis axis.

Alternatively, and in a second embodiment shown in FIG. 7, the coordinate system for the measurement of vertebral morphology may be established by creating a column averaged histogram 104 taken along line 46 in the scan direction 19. The vertical axis of the column averaged histogram is a line number of a row of data elements, and the horizontal axis of the column averaged histogram is the total density of the data elements of that row, that is, the sum of the data element in that row. For a vertebrae 20 tipped with respect to the scan direction 19, the column averaged histogram 104 will exhibit a relatively low rate of change as a result of the obliquely advancing rows of data elements extending arrow 106 which crossing the inferior border 36 and superior border 34 at an angle. In a manner similar to that described with respect to FIG. 6, a new column axis 108 is iteratively generated and canted with respect to the scan direction 19 by an angle φ. A new column averaged histogram 104' is generated with respect to this column axis 108. If the row orientation 106' of the new column axis 108 better aligns with the inferior border 36 and the superior border of the vertebral body 21, the column averaged histogram 104' will exhibit a more rapid rate of change in total row bone density with respect to row number. The derivative of the column averaged histogram 104' may be taken and the peak value of the derivative compared between column averaged histograms 104 with other column axes 108 (at different angles φ) to select a column axis 108 that produces the greatest such derivative value within a limited angular range. This column axis 108 is selected as the reference axis for future morphological measurements.

Thus, although the scan direction 19 may not be aligned with the vertebral body 21, so that the anterior and posterior borders 30 and 32 are substantially parallel to the scan direction 19 and the superior border 34 and inferior border 36 substantially perpendicular to the scan direction 19, a new column direction 108 may be determined and measurements of the vertebrae morphology taken with respect to that column direction 108 to provide improved accuracy and repeatability in the measurement of the vertebrae morphology. This alignment of a coordinate system represented by column axis 108 to each vertebra is indicated at process block 68 of FIG. 5.

Figure 8:
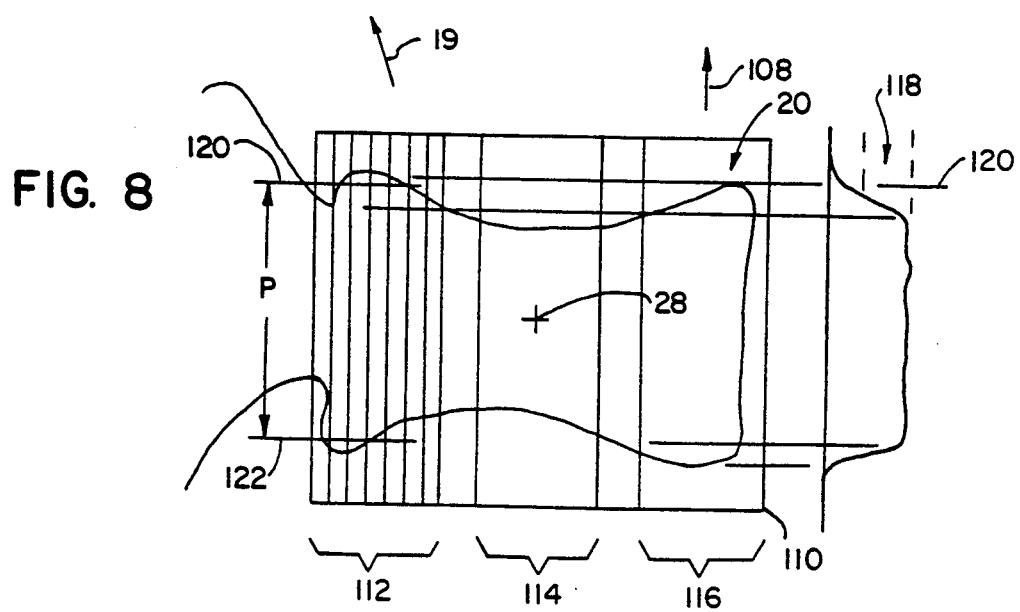
FIG. 8 is a lateral view of a vertebra aligned with the analysis axis showing the generation of measurement zones over which vertebral height is averaged in preparation to analyzing the morphometry of the vertebra.

Referring now to FIG. 8, in general, the column direction 108 will differ from the scan direction 19. Once the column direction 108 has been determined for a given vertebral body 21, the data elements are effectively "rebinned" to comport with that new coordinate system. The rebinning may be accomplished by generating a new series of locations within the vertebral body 21 corresponding to evenly spaced lines and columns aligned with the new column axis 108. Interpolated data elements lying on these locations at the new columns and rows are obtained by a bilinear interpolation of the nearest neighbor actual data elements weighted according to the actual locations of those data elements. New vertical and horizontal histograms are then constructed from these interpolated data elements much in the manner as described with respect to FIG. 6 with the horizontal histogram displaying average density for a vertical column of interpolated data elements and the vertical histogram displaying the average density for a row of the interpolated data elements.

Referring to FIG. 8, the minima of the horizontal and vertical histograms are used to derive an analysis rectangle 110 in the same manner as that described with respect to the rectangle 100 of FIG. 6, the analysis rectangle 110 being aligned with the column axis 108 and encompassing principally the vertebral body 21 and not the posterior elements 38. This analysis rectangle 110 is then divided by the computer into zones as indicated by process block 68 of FIG. 5. In the preferred embodiment, three zones are selected, a posterior zone 112, a medial zone 114 and an anterior zone 116. In the preferred embodiment, the zones are rectangular having an anterior to posterior width of ¼ that of the analysis rectangle 110 and extending the full height of the analysis rectangle 110 in the superior to inferior direction and evenly spaced therein. The relative width and number of zones is arbitrary and can be varied according to the needs of the user and the dimensions of the analysis rectangle 110.

In the example of FIG. 8, the posterior, medial and anterior zones define a set of data elements that will be employed to produce fiducial measurements with respect to the morphology of the vertebral body 21. The first set of such measurements is to determine the average height of that portion of the vertebral body in the superior to inferior direction of each of the three zones of the analysis rectangle 110.

In one embodiment, this is done by starting with the posterior zone 112; the data elements within the zone are automatically summed across rows by the computer to produce a zone histogram 118. The vertical axis of the zone histogram 118 is a row number of data elements corresponding to an anterior-posterior row and the horizontal axis is the total bone mass of the data elements of that row and within the posterior zone 112. This zone histogram 118 differs from the others histograms described thus far in that it is effectively focused on the posterior zone 112 and thus sensitive to the morphology of that region alone.

A first row 120 is automatically identified by the computer on that histogram, and thus with respect to the vertebral body 21, at the rising edge of the histogram 118 associated with the superior border 34 in the posterior zone 112. A number of criteria may be employed in selecting this first row 120, such as, the first row having a bone mass value to exceed a fixed predetermined threshold. In the preferred embodiment, the row is selected as that which has a PBM value first exceeding 30% of the peak histogram value of the zone histogram 118. Ideally, the computer selects as a first row 120 the row which best approximates the position of the superior border 34 if the position of its contour in the posterior zone (as weighted by PMB value) were averaged out. In actual practice a deviation of the selected first row 120 from the true average of the superior border 34 is not significant as long as the same criteria is used each time in selecting the first row 120 and hence constancy of measurement is obtained.

Likewise, a second row 122 is selected from the histogram 118 in its inferior border 36 in the posterior zone 112. Here the falling edge of the histogram 118 is examined and the second row 122 selected as that row which first falls below 30% of the maximum PBM value for the histogram 118. The distance between these columns 120 and 122 is automatically determined and termed the posterior height and represented by P and is assumed to be the average height of the vertebral body in the region of the posterior zone.

Each of the other zones, the medial zone 114 and the anterior zone 116 are likewise analyzed by generating a zone histogram 118 and identifying two rows, one at the superior border 34 and one at the inferior border 36. The distance between these columns for the medial zone becomes the medial height M and for the anterior zone becomes the anterior height A. The extractions of these morphological height values is indicated in FIG. 5 as process block 70.

In the preferred embodiment, the height values A, M, and P are calculated by multiplying the number of rows of data elements between the first row 120 and the second row 122 for each zone by the distance between each row of data elements in the analysis rectangle 110. That distance between rows of data points is a characteristic of the digital imaging technique used, and will be known. The computer will automatically perform the above described analysis on each zone of the analysis rectangle.

Figure 9:
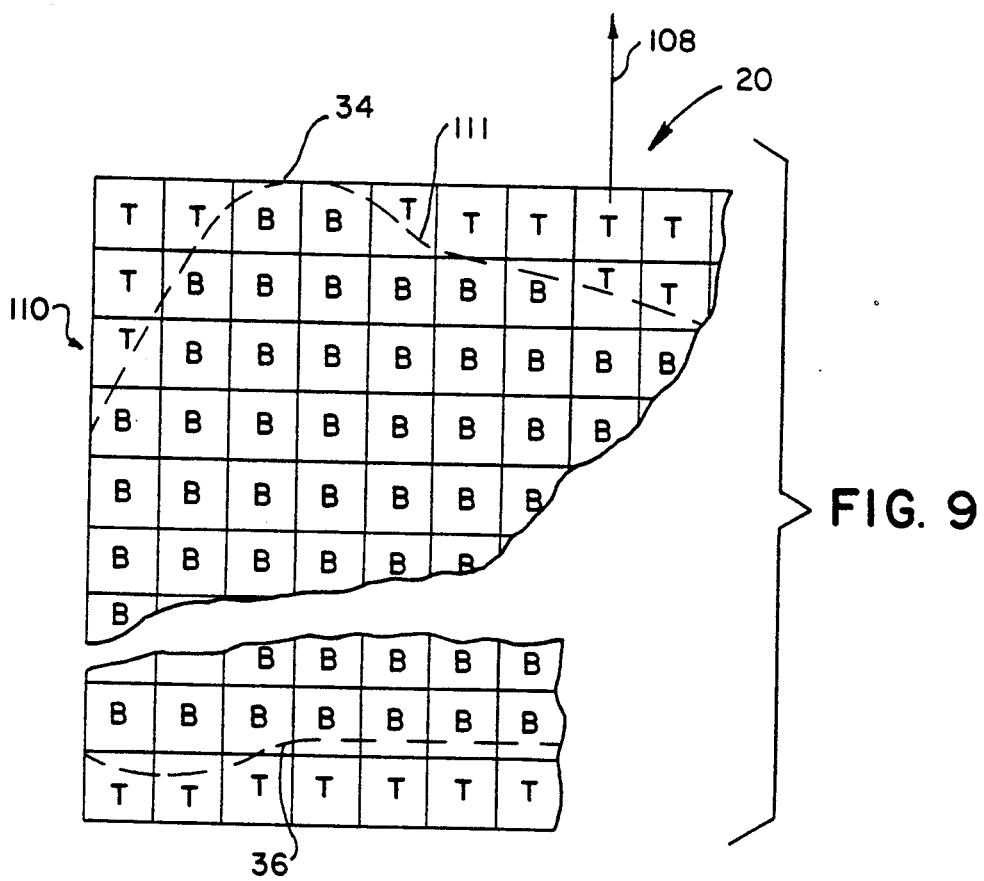
FIG. 9 is a schematic diagram of the bone mineral density values over a portion of a vertebra illustrating one method of determining the borders of a vertebra wherein for clarity the density values within a range associated with tissue are shown by the letter "T" and the density values in a range indicating bone are shown by the letter "B"

In an alternative embodiment, the average height of each zone is determined by the computer by automatically identifying in each zone, data pairs; one data element of each pair corresponding to a location on the superior border and the other data element corresponding to a location on the opposite, inferior border. The two data elements of each pair have a relationship to one another such that an imaginary line transecting each data element of a data pair would be reasonably parallel to the column axis 108. Each data element of a data pair is selected by the computer by performing a local comparison of the PBM values of data elements. For example in selecting data elements lying on the superior border, the computer would examine the PBM values of adjacent elements. As illustrated in FIG. 9 a data element 111 having neighboring data elements of similar value in the anterior, posterior and inferior orientations but of markedly lesser value in the superior orientation would be assumed to lie at or near the superior border. In like manner the computer will automatically examine all the data elements in the top ⅓ position of zone 112 to determine those data elements lying on the superior border. Once data elements on the superior border had been selected, a similar analysis would be conducted on the data elements in the lower ⅓ portion of zone 112 to select data elements lying on or near the inferior border portion of zone 112. With data elements selected on each border the computer would then pair data elements on the superior border with data elements on the inferior border by assigning the data elements to columns reasonably parallel to column axis 108. Having organized the data elements into pairs and assigned the pairs to columns the computer employs an algorithm to automatically determine the distance between each element in a pair by multiplying the number of data elements found between each element of a data pair by the distance between each data element. As stated above the distance between data elements is a characteristic of the digital imaging technique used. The distance between data elements of a pair is taken as the inferior to superior height of the vertebral body 21 at the particular location of the column associated with that pair.

Having determined the height of all the columns in zone 112, the heights are summed and an average height is obtained for zone 112. In similar fashion average heights are obtained for the medial zone 114 and the anterior zone 116.

By a similar process, the analyses rectangle 110 may be divided in to several (preferably three equal) horizontally extending fiducial zones (not shown) and columns identified at the anterior and posterior borders 30 and 32 of the vertebral body 21 to determine the average widths of such horizontally extending fiducial zones. In the preferred embodiment, three zones, a superior zone S, central zone C and inferior zone I are selected and automatically measured.

In each zone S, C and I, an anterior column and a posterior column is identified in a process analogous to that described above with respect to the selection of the first and second rows 120 and 122 of a posterior zone 112, a medial zone 114 and an anterior zone 116. A center column is also determined for the zones S, C and I being exactly half way between the anterior and posterior identified columns. The intersection of the identified columns of the zones S and I and the rows posterior zone 112, a medial zone 114 and an anterior zone 116 define a set of fiducial points. For example, the intersection of the first row 120 for the posterior zone 112 and the first column for zone C defines one such fiducial point.

The identified columns of the zones S, C and I also serve to create measures S, C, and I corresponding to measures A, M, and P, as described above, but extending in a anterior posterior direction.

Thus it will be understood that fiducial points at the "corners" and center superior and inferior borders 34 and 36 of the vertebral body 21 may be established and that the separation of these fiducial points with respect to one another measured automatically. Although each of these fiducial points has a specific location, they represent an average of the BMD values of the surrounding data points and hence are robust against small errors in the BMD measurements at any given data point.

Once the computer has identified these fiducial points, the computer automatically uses this data to accurately define the shape and size of the vertebra being studied which, at the option of the operator can be displayed visually such as on a CRT device or a printing device. More importantly, however, the computer is programmed to use the data regarding shape and size to formulate indicia of vertebral condition having clinical or diagnostic value and then to visually display the indicia for use by the operator either in diagnosing a clinical condition or increasing the accuracy of bone density measurements if such measurements are being made.

Using the invention described herein, measurements can be automatically obtained for a single vertebra, or can be obtained for several vertebrae. It is possible to use the analysis performed by the algorithm for several purposes. This analysis is most effectively directed to the vertebral body, that is the portion of the vertebra excluding the posterior element. Various measurements of a vertebral body which are obtained by the invention herein described can be used to provide indicia of disease or deformity as described below. Additionally, the measurements obtained of a single vertebral body can be compared to those of adjacent vertebral bodies, as determined from a single scan, to determine if one or more vertebra has been subjected to a trauma or other incident which produces an abnormality in that vertebra. Alternatively, the indicia of a vertebral body can be compared to those obtained from a normal reference population, to determine aberrant or abnormal vertebrae, either singly or collectively, in a given patient. Such normative results may be adjusted for body height, sex, and weight of the individual patient, as well as for maturity of the individual. Another alternative is that the indicia for the vertebral bodies can be compared from time to time in the same individual, to show changing vertebral morphology over time, which can be indicative of the progress of clinically significant conditions.

EXAMPLE 1: ANTERIOR HEIGHT

A particular indicia of interest for vertebra morphology is anterior height of the vertebra. It has already been described above, in connection with the description of the fiducial points, how the algorithm automatically calculates the distance from inferior border to superior border for each fiducial zone. The anterior height of the vertebral body is the distance between the two end plates, or the distance between the superior border and the inferior border at or adjacent to the anterior border. In the prior art, the point at which the anterior height of the vertebra was preferably measured was within the first 5 to 10 mm from the extreme anterior border of the vertebral body. In the preferred embodiment of the present invention a fiducial zone 116 is selected which occupies the anterior ¼ portion of the analysis rectangle 110 and within this zone the computer determines an average height of the anterior portion of the vertebral body 21. If compared with the prior art technique of selecting a particular point for measurement of anterior height, the technique of the present invention which automatically determines an average height within a preselected fiducial zone is found to be superior in terms of reproducibility. This anterior height A, as determined by the present invention, may be displayed to an operator in absolute units of measurement, such as millimeters, or the computer can provide height relative to the average height either of normal values of vertebrae in the general population or the other vertebrae of that patient.

EXAMPLE 2: POSTERIOR HEIGHT

Another indicia of interest is the measurement of posterior height P of the vertebra. Like anterior height, posterior height measurements made in the prior art are taken at a single location within 5 to 10 mm of the posterior border of the vertebra. The present invention provides an automatic measurement of the average height of the posterior region of the vertebral body 21 lying within the posterior fiducial zone 112 which occupies the posterior ¼ of the analysis rectangle 110. Like anterior height, posterior height may be displayed to an operator in absolute units of measurement, such as millimeters, or the computer can provide height relative to the average height either of normal values of vertebrae in the general population or the other vertebrae of that patient.

EXAMPLE 3: ANTERIOR/POSTERIOR HEIGHT COMPARISON

An important indicia which the computer can be programmed to automatically obtain is a comparison of anterior height A to posterior height P. Typically a 15% decrease in anterior vertebral height, either relative to a norm, relative to the same individual in previous measurements, or relative to the posterior height of the same vertebra, is taken as an index of anterior vertebral fracture, a clinically significant indication.

EXAMPLE 4: WEDGE ANGLE

Another indicia of vertebral morphology which can be automatically obtained with the present invention is the wedge angle. The wedge angle of the vertebra is defined as the degree of departure from a parallel relationship that linear extensions of the planes of averages of the inferior and superior borders would create. In the prior art, this is calculated based on the overall anterior and posterior height of the vertebra. From these values of anterior and posterior height and from the distance between the locations at which the measurements were taken, it becomes possible to calculate the angle between hypothetical straight lines extending through the superior and inferior borders of the vertebra. In the present invention, the distance between A and P for purposes of plotting the wedge angle is C. Since A, P and C are average values, variability in the wedge angle due to variation in the selection of the location for height and width measurement is avoided. Typically a 15° wedge angle of a vertebra is taken to indicate that wedge fracture has occurred in the vertebra. A wedge fracture is a recurrent clinical condition, observed as a modality of vertebral fracture recognized in clinical literature.

EXAMPLE 5: BICONCAVITY INDEX

Another indicia of vertebral morphology which the computer of the present invention can be programmed to automatically measure is referred to as the biconcavity index. The index of biconcavity of the vertebral body is calculated by comparing the degree to which the height of the central portion of the vertebral body deviates from the average height of the posterior and anterior borders of the body. In other words, this is measuring the deformation of the vertebral body as it tends to become a concave object. This biconcavity indicates a degree of deformation of the vertical body associated with relatively poor vertebral condition. This quantity can be calculated automatically by the computer which uses an algorithm to compare M to the average of A and P. M can also be compared to adjacent vertebrae, or to average values from a normal reference population previously obtained. A 15% preferential decrease in central height of the vertebral body as compared to the anterior and posterior borders, is often taken to represent a central fracture or a condition of biconcavity.

EXAMPLE 6: HYPERTROPHY

Another indicia of vertebral morphology which the computer of the present invention can be programmed to measure is hypertrophy of the endplates of the vertebrae or hypertrophy of nodes located within the vertebra. Hypertrophy refers to a condition where portions of the vertebral body have a relative density which is abnormally greater than that typically seen with other vertebrae. In conventional densitometry, localized areas of high or low density are ignored and only larger area averages are obtained. This can lead to misleading interpretations of bone mineral levels when discontinuities are present as caused by hypertrophy. The ability of the present invention to define and reproducibly locate a variety of zones: the posterior zone 112, the medial zone 114, the anterior zone 116 and zones S, C, and I, allow bone density to be evaluated separately at a variety of places within the vertebra. By comparing the bone density in S or I zones to the C zone, for example, endplate hypertrophy may be detected. Alternatively, a hypertrophied node, may be detected by evaluating the bone density over the entire region within the fiducial points at the "corners" of the vertebra to identify any data points, or a small set of data points, within that defined area that have values which differ by more than a predefined amount from the statistical norm of all the values within that area.

While this indicia is not generated specifically for clinical value, in and of itself, it is useful insofar as it represents information about a region of vertebra having unique characteristics which must be excluded from otherwise valid measurements of bone density or mineral content. For this reason, it may be used to provide a warning to the operator indicating that the bone mineral data for a particular vertebra may need close review.

EXAMPLE 7: INTERVERTEBRAL SPACING

Intervertebral spacing may be readily determined from the evaluation of the fiducial points at the superior border of one vertebra and the inferior border of the next superior vertebra. Essentially, the intervertebral spacing is the distance between the corresponding fiducial points for these two vertebrae.

As a result of the possible difference in column axes 108 for the two vertebrae, the intervertebral distance may preferably be evaluated by considering the average distance between two edges, one defined by line segments joining the fiducial points at the superior border of the inferior vertebra, and the other defined by line segments joining the fiducial points at the inferior border of the superior vertebrae.

EXAMPLE 8: WARNING OF DEFECTIVE VERTEBRA

It is specifically intended that the indicia of morphological character of the vertebral body, whether height, compression, wedge, or biconcavity, are utilized by the instrument for two discreet purposes. One purpose is to create a warning to the operator that the bone mineral density data for a particular vertebra should not be utilized since it may be inappropriate. It can readily be understood that a porous bone if crushed will have a higher measured density than a porous bone which has not been subject to crushing. In that instance, the higher density of the crushed bone is not an indication of the health of that bone, quite to the contrary. Accordingly, it is appropriate for the instrument of the present invention to create an indicational warning to the operator as indicated by process block 76 in FIG. 5 in when one or more of the indicia of significant vertebral body fracture have been detected. In any event, the result is that a heightened accuracy of bone mineral density calculation is obtained by the bone densitometer, as well as providing the benefit of potential diagnosis of clinically significant conditions of vertebral deterioration.

The calculation of these various indicia from the measurements of A, M, and P, and S, I and C and their separation is indicated in process block 72 of FIG. 5. At subsequent process block 76 an indication may be presented to the operator of abnormal indications which have been detected by the method, if any. The abnormal conditions can be indicia described above which are outside the normal values to be expected for patients of the category of the patient who has been scanned. If such an indication has occurred, the operator will then know that the average value for bone density for the particular vertebrae having the discontinuity should not be utilized for clinical purposes.

EXAMPLE 9: PREDICTING VERTEBRAL FRACTURE

A decrease in bone mass, or the presence of one or more vertebral fractures, is associated with an increase in the likelihood of future vertebra fractures. A decrease in bone mass of two standard deviations is associated with an increase of four to six times in the likelihood of future vertebral fractures whereas the existence of two fractures, as determined by a morphologic measurement of anterior height or A is associated with an increase of twelve times in the likelihood of future vertebral fractures. See, Ross, et al., "Pre-Existing Fractures and Bone Mass Predict Vertebral Fracture Incidence in Women", *Annals of Internal Medicine*, v.114–11:919 (1991).

A combination of bone mass measurement and morphometric evaluation of fracture is associated with an increase of seventy-five times in the likelihood of future vertebral fractures and provides correspondingly improved predictive power. The present invention, which allows a densitometer to be used in making morphometric measurements, should prove valuable in conveniently providing both bone mass and fracture data for such combined measurements.

EXAMPLE 10: DUAL ANGLE MORPHOLOGY AND BMD MEASUREMENT

Figure 10:
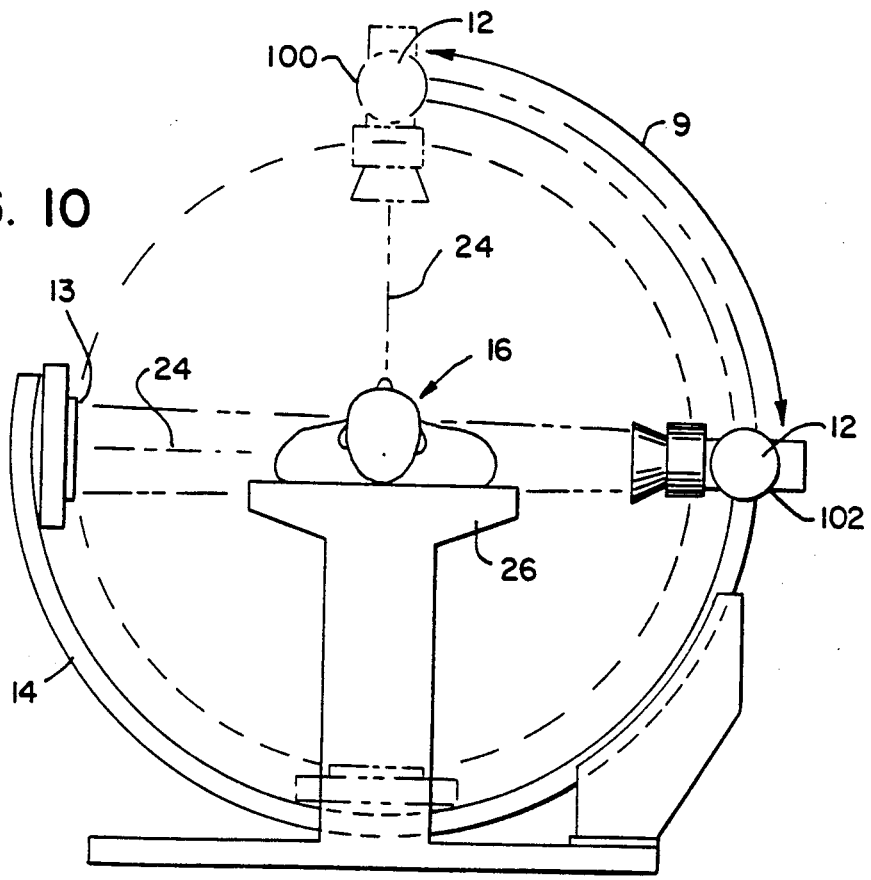
FIG. 10 is a view of the instrument of FIG. 1 along the scanning direction showing movement of the source and detector between a lateral position and an anterior posterior position as performed in one embodiment of the present invention.

Referring to FIG. 10, prior to the lateral scan of the patient 16, an anterior posterior dual energy scan may be performed with the x-ray source 12 in position 100 as rotated about the patient 16 on C-arm 14. As is understood in the art, dual energy scanning provides an improved ability to distinguish between x-ray attenuation caused by tissue as opposed to bone allowing more accurate BMD determinations, but also provides less accuracy for morphology measurements. The anterior posterior positioning of the C-arm 14 also improves the bone density measurement to the extent that the amount of intervening tissue is reduced at that angle.

Referring also to FIG. 5 the BMD values obtained from the anterior to posterior scan may be employed to calculate BMD as indicated by process block 78 and to calculate bone area as indicated by process block 80 according to techniques well known in the art. Rather than directly displaying the BMD values however, a lateral scan is then performed with the x-ray source 12 at position 100 so that the axis of radiation 24 is horizontal. The calculated values of BMD for various points in the anterior posterior scan of the patient may be matched approximately to those corresponding points in the lateral scan and the indicia of the morphometric measurements of a given vertebra 20 may be matched to the calculated BMD values of process block 80 and bone area values of process block 82. If the indicia for a given vertebra are abnormal, then at process block 84, where BMD and area calculations may be displayed, a suitable warning may be given to the operator that the BMD values and area values are suspect as indicated by process block 76.

The correlation of anterior to posterior scanned points to lateral scanned points simply matches the longitudinal coordinates of each such point and makes the assumption that the patient has not shifted on the table appreciably between scans. Alternatively, the intervertebral zones 40 may be derived for each of the anterior posterior and lateral scans and the data from each scan shifted to correlate the histograms of each scan so that the intervertebral zones 40 match.

The ability to use a densitometer to make morphologic measurements is critical to this augmentation of BMD and bone area calculations by morphometric indicia as it allows both measurements to be made without shifting the patient.

It is thus envisioned that the present invention is subject to many modifications which will become apparent to those of ordinary skill in the art. Accordingly, it is intended that the present invention not be limited to the particular embodiment illustrated herein, but embraces all such modified forms thereof as come within the scope of the following claims.

The indicia calculated at any one time for a patient may be compared to subsequent or previous determinations on the same patient. By such comparison, changes in vertebral morphology over time can be tracked. In addition, the digital image obtained at subsequent determinations following an initial determination may be subtracted from the stored initial image to produce a differential image. The boundary conditions used for determining morphological indicia may be used to precisely overlap such sequential images.

I claim:

1. A bone densitometer for scanning a vertebra of an animal or human with x-rays so as to obtain information about the bone character of said vertebra, said vertebra having superior, inferior, anterior and posterior borders, said information being derived from a matrix of discrete data elements each having a value related to a physical characteristic of the material of the vertebra comprising:
    a) a digital computer for incorporating the following means:
        1) means receiving the matrix of discrete data elements and reviewing the values of the data elements and their defined locations to identify the following:
            a) a coordinate aligned with the inferior and superior borders;
            b) at least two morphometric fiducial points;
        2) a means for using two or more of said morphometric fiducial points to make at least one morphological measurement of said vertebra;
    b) a means for outputting said morphological measurement from said digital computer.

2. A densitometer as described in claim 1, further comprising a means for using said morphological measurement to automatically determine whether at least one indicia associated with clinical condition is present and a means for warning an operator if at least one indicia associated with a clinical condition is present.

3. A densitometer as described in claim 2 wherein said means for warning an operator is a message outputed from said digital computer.

4. A densitometer as described in claim 1, further comprising a fan beam x-ray and a linear array detector.

5. A densitometer as described in claim 2, further comprising:
    a) a means whereby said digital computer determines from the data elements of said matrix at least one measure of bone character of said vertebra, said one measure of bone character being related to the bone mineral of the vertebra;
    b) a means for outputting from said digital computer at least one measure of bone character of said vertebra.

6. A densitometer as described in claim 5 wherein said x-rays are dual energy x-rays.

7. A densitometer as described in claim 6, further comprising a means to switch from dual energy x-rays to single energy x-rays.

8. A densitometer as described in claim 5, further comprising a means for obtaining an anterior-posterior or lateral scan of said vertebra without repositioning said human or animal.

9. A bone densitometer for scanning the vertebra of an animal or human with radiation to obtain information about the bone character of a vertebra in an animal or human, said vertebra having a superior, inferior, anterior and posterior border, said information being derived from a first and second matrix of discrete data elements each having a value wherein each said data element corresponds to a defined location in said vertebra, and wherein the value of each data element is related to a physical characteristic of the material of the vertebra, the densitometer comprising:
    a) a means for positioning a radiation source and detector in opposed relationship about a vertebra for directing radiation along an axis through the vertebra and detecting its attenuation to produce the first and second matrix of data elements;
    b) a positioning means for rotating the axis between a first and second angle about said vertebra so that said first matrix of discrete data elements is acquired at the first angle and said second matrix of discrete data elements is acquired at the second angle;
    c) a digital computer means for the following:
        1) for receiving and analyzing said first matrix of data elements to determine bone character measurements for said vertebra;
        2) receiving and reviewing said second matrix of data elements to identify at least one pair of fiducial points of said vertebra and to calculate morphological measurements using said fiducial points;
    d) a display means for outputting from said digital computer said bone character measurements and morphological measurements.

10. A densitometer as described in claim 9, further comprising a means for using said morphological measurements to automatically determine whether at least one indicia associated with a clinical condition is present and a means for warning an operator if at least one indicia associated with a clinical condition is present.

11. A densitometer as described in claim 9 wherein said radiation is dual energy x-ray radiation.

12. A densitometer as described in claim 1 wherein said radiation source produces a fan beam of x-rays and said detector is a linear array detector.

13. A densitometer as described in claim 11 wherein the first angle is along an anterior to posterior axis and said second angle is along a lateral axis through said vertebra.

14. A densitometer as described in claim 13 further comprising a means to switch from dual energy x-rays to single energy x-rays.

15. A densitometer as described in claim 14 further comprising a K-edge filter to produce said dual energy x-rays and wherein said switching means comprises a means for removing said K-edge filter.

16. A densitometer as described in claim 13 further comprising an array detector which is comprised of a first detector sensitive to one energy level of said dual energy x-rays and a second detector sensitive to the other energy level of said dual energy x-rays, and wherein said switching means comprises a means for switching from sampling both first and second detectors to sampling one of said first and second detectors.

17. A method for determining vertebral morphology using an x-ray bone densitometer wherein said bone densitometer is made to scan a vertebra of an animal or human to obtain information about the bone character of said vertebra, said vertebra having a superior, inferior, anterior and posterior border, and said information being derived from a matrix of discrete data elements each having a value wherein each said data element corresponds to a defined location in said vertebra, and wherein the value of each data element is related to a physical characteristic of the material of the vertebra, and wherein said bone densitometer has a digital computer means for receiving said matrix, said method for determining vertebral morphology comprising the steps of:

a) causing said digital computer means to review the values of data elements and their defined locations to identify the following:
   1) a coordinate aligned with the inferior and superior borders;
   2) two or more morphometric fiducial points;

b) causing said digital computer to make at least one morphometric measurement using said two or more fiducial points;

c) causing said morphometric measurement to be output from said digital computing means.

18. A method for determining vertebral morphology using a bone densitometer as described in claim 17, further comprising the steps of comparing said morphometric measurement to a previously selected standard and using the results of said comparison to determine whether at least one indicia associated with a clinical condition is present.

* * * * *